United States Patent [19]

Stack et al.

[11] Patent Number: 4,968,792

[45] Date of Patent: Nov. 6, 1990

[54] PSYCHOTROPIC BENZISOTHIAZOLE DERIVATIVES

[75] Inventors: Gary P. Stack, Ambler; Magid A. Abou-Gharbia, Glen Mills, both of Pa.; Thomas D. Golobish, Princeton, N.J.

[73] Assignee: American Home Products Corporation, New York, N.Y.

[21] Appl. No.: 412,256

[22] Filed: Sep. 25, 1989

[51] Int. Cl.$^5$ .................. C07D 417/14; A61K 31/425
[52] U.S. Cl. ..................................... 540/524; 540/520; 540/461; 540/463; 548/368
[58] Field of Search ............... 540/461, 463, 520, 524; 544/368

[56] References Cited

U.S. PATENT DOCUMENTS

| | | | |
|---|---|---|---|
| 4,411,901 | 10/1983 | Temple et al. | 544/368 |
| 4,452,799 | 6/1984 | Temple et al. | 544/368 |
| 4,656,173 | 4/1987 | Yevich et al. | 544/368 |
| 4,732,983 | 3/1988 | Stack et al. | 544/295 |
| 4,745,117 | 3/1988 | Ishizumi et al. | 544/368 |
| 4,797,488 | 1/1990 | Stack et al. | 544/295 |

FOREIGN PATENT DOCUMENTS 2181731  10/1985  United Kingdom ................ 544/295

*Primary Examiner*—Robert T. Bond
*Attorney, Agent, or Firm*—Walter Patton

[57] ABSTRACT

Disclosed herein are novel benzisothiazole derivatives having pharmacological activity, to a process for preparing them, to pharmaceutical compositions containing them, and to their use in the treatment of a variety of central nervous system disorders.

8 Claims, No Drawings

PSYCHOTROPIC BENZISOTHIAZOLE DERIVATIVES

BACKGROUND OF THE INVENTION

U.S. Pat. No. 4,411,901 and related divisional U.S. Pat. No. 4,452,799 disclose a series of benzisothiazole and benzisoxazole piperazine derivatives having selective antipsychotic activity.

U.S. Pat. No. 4,656,173 discloses the antipsychotic activity of a benzisothiazole S-oxide derivative.

Great Britain Patent No. 2,181,731-A discloses fused N-substituted bicyclic imides useful as antipsychotic and/or anxiolytic agents.

U.S. Pat. No. 4,797,488 discloses N-(aryl and heteroarylpiperazinylalkyl)polycyclic-1,3-dicarboxylic acid imides useful as antipsychotic and/or anxiolytic agents.

U.S. Pat. No. 4,732,983 discloses antipsychotic and/or anxiolytic N-(aryl and heteroarylpiperazinylalkyl)-polycyclic dicarboxylic acid imides.

DESCRIPTION OF THE INVENTION

In accordance with this invention, there is provided a group of antipsychotic/anxiolytic agents of the formula:

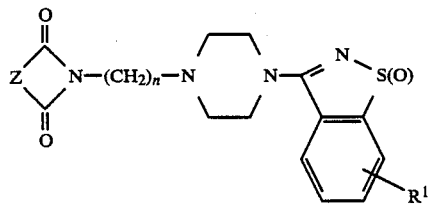

wherein $R^1$ is hydrogen, hydroxy, cyano, alkyl of 1 to 3 carbon atoms, alkoxy of 1 to 3 carbon atoms, halo or trifluoromethyl; (O) represents optional oxidation of sulfur; n is 2 to 5 and Z is

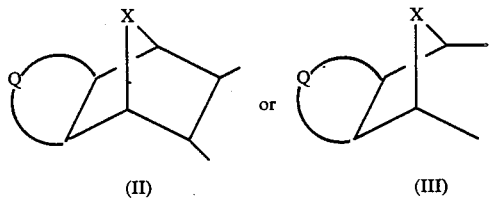

wherein X is alkylene of 1 to 4 carbon atoms or alkylidene of 2 to 4 carbon atoms; Q is alkylene of 1 to 4 carbon atoms, alkylidene of 2 to 4 carbon atoms, or

or Z is

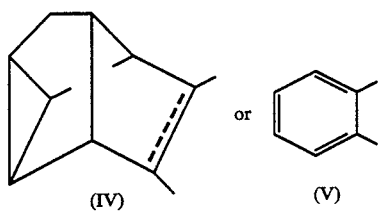

or a pharmaceutically acceptable salt thereof.

Of these compounds of formula (I), the preferred members are those in which $R^1$ is hydrogen, hydroxy, methoxy, bromo or chloro; n is 4; Z is (II) wherein X is ethenylene and Q is methylene or ethenylene; or Z is (III) wherein X is methylene and Q is

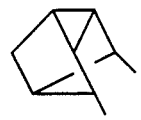

or Z is (IV) or (V) or a pharmaceutically acceptable said thereof.

Still further preferred compounds are designated:
decahydro-3-[4-[4-(1,2-benzisothiazol-3-yl)-1-piperazinyl]butyl]-1,5-methano-6,7,9-metheno-2H-pentaleno[1,2-d]azepine-2,4(3H)-dione;
2-[4-[4-(1,2-benzisothiazol-3-yl)-1-piperazinyl]butyl]-3a,4,4a,6a,7,7a-hexahydro-4,7-etheno-1H-cyclobut[-f]isoindole-1,3(2H)-dione;
2-[4-[4-(1,2-benzisothiazol-3-yl)-1-piperazinyl]butyl]-4,4a,5,5a,6,6a-hexahydro-4,6-ethenocycloprop[-f]isoindole-1,3(2H,3aH)-dione;
2-[4-[4-(1,2-benzisothiazol-3-yl)-1-piperazinyl]butyl]-1H-isoindole-1,3(2H)-dione;
(exo)-octahydro-2-[4-[4-(1,2-benzisothiazol-3-yl)-1-piperazinyl]butyl]-4,5,7-metheno-1H-pentaleno[1,2-c]pyrrole-1,3(1H)-dione;
(endo)-octahydro-2-[4-[4-(1,2-benzisothiazol-3-yl)-1-piperazinyl]butyl]-4,5,7-metheno-1H-pentaleno[1,2-c]pyrrole-1,3(2H)-dione;
and the pharmaceutically acceptable salts thereof.

The pharmaceutically acceptable salts are those derived from such organic and inorganic acids as: acetic, lactic, citric, tartaric, succinic, maleic, malonic, hydrochloric, hydrobromic, phosphoric, nitric, sulfuric, methanesulfonic, and similarly known pharmaceutically acceptable acids.

The compounds of this invention are prepared by conventional methods. For example, a polycyclic 1,2- or 1,3-dicarboxylic acid or anhydride derived therefrom is refluxed with the desired benzisothiazolyl piperazinyl alkylamine in dry pyridine, toluene or xylene. Water removal may be achieved by either chemical (e.g. ethoxyacetylene) or mechanical (e.g. Dean-Stark trap) means.

The polycyclic dicarboxylic acids themselves are known compounds or they can be prepared from the appropriate polycyclic olefin by treatment with a suitable oxidizing agent such as potassium permanganate or ruthenium tetroxide (or from the appropriate polycyclic ketone by treatment with potassium permanganate or potassium trioxide or from the appropriate diketone via treatment with periodic acid). These procedures may be illustrated as follows:

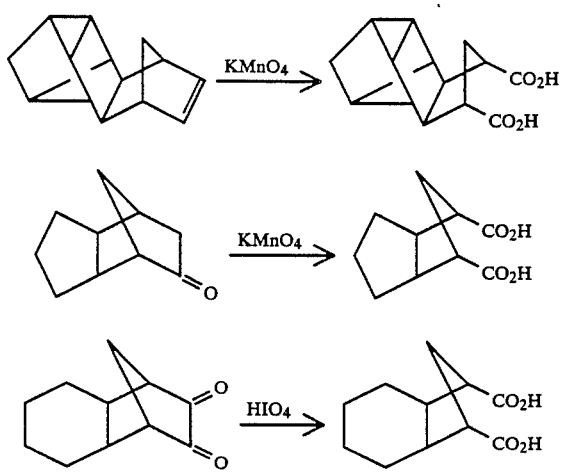

Alternatively, the compounds of this invention are readily prepared from the analogous polycyclic imide via alkylation with a suitable dihalo-lower-alkane in the presence of a strong base such as sodium hydride followed by reaction of the intermediate product with the desired benzisothiazolyl piperazine, thusly:

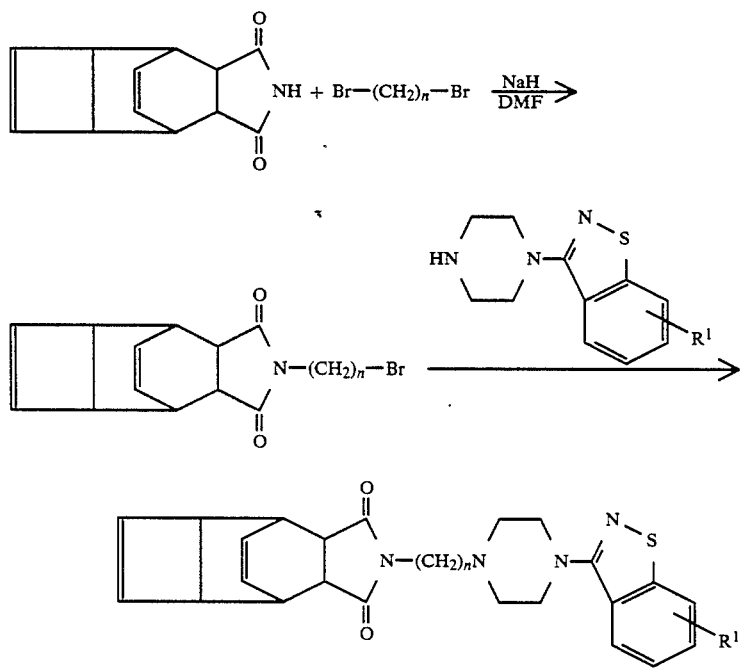

wherein n and $R^1$ are as defined above.

Compounds of formula (I) which bear the optional oxidation state of sulfur may be conveniently prepared from the corresponding divalent sulfur-containing compounds. While various oxidative preparatory methods may be employed, it was found most convenient to effect the oxidation at low temperatures with mixed sulfuric and nitric acids.

The compounds of this invention possess high affinities for the dopamine D-2 receptor and the serotonin 5-HT$_{1A}$ receptor, and consequently, they are useful as antipsychotic and anxiolytic agents for the treatment of a variety of central nervous system disorders such as schizophrenia, anxiety, sleep disorders, and related problems.

High affinity for the dopamine D-2 receptor was established by the standard experimental test procedure of Fields, et al., Brain Res., 136, 578–584 (1977) and Yamamura et al., eds., Neurotransmitter Receptor Binding, Raven Press, N.Y. (1978) wherein homogenized limbic brain tissue is incubated with $^3$H-spiroperiodol and various concentrations of test compound, filtered and washed and shaken with Hydrofluor scintillation cocktail (National Diagnostics) and counted in a Packard 460 CD scintillation counter. The results of this testing with compounds representative of this invention are given below.

High affinity for the serotonin 5-HT$_{1A}$ receptor was established by testing the claimed compound's ability to displace [$^3$H]8-OHDPAT (dipropylaminotetralin) from the 5-HT$_{1A}$ serotonin receptor following the procedure of Hall et al., J. Neurochem. 44, 1685 (1985). This procedure is employed to analogize this property of the claimed compounds with that of buspirone, which is a standard for anxiolytic activity, and, like the compounds of this invention, displays high affinity for the 5-HT$_{1A}$ serotonin receptor subtype. The anxiolytic activity of buspirone is believed to be, at least partially, due to its 5-HT$_{1A}$ receptor affinity (Vander Maelen et al., Eur. J. Pharmacol., 129 (1–2) 123–130 (1986).

The results of the two standard experimental test procedures described in the preceding two paragraphs were as follows:

| Compound | D-2 Binding (Inhibition at 1 μM) | ($K_i$, nM) | 5-HT$_{1A}$ Binding (Inhibition at 1 μM) | ($K_i$, nM) |
|---|---|---|---|---|
| Example 3 | 99% | | 100% | — |
| Example 4 | 95% | | 97% | 0.65 |
| Example 5 | 95% | 0.50 | 96% | 0.065 |
| Example 6 | 100% | | 100% | — |
| Example 7 | 100% | | 100% | 0.4 |

The antipsychotic properties of the compound of Example 5 were further established by standard pharmacologically accepted procedures involving conditioned avoidance studies in which trained male CD rats (Charles River), 400–500 g. body weight are exposed to a fifteen second warning tone (conditioned stimulus) continued for an additional fifteen seconds accompanied by electric shock. The rat can avoid the electric shock by jumping to an exposed shelf (shelf-jump response). A response during the initial warning tone is considered an avoidance response, while a response during shock delivery is considered an escape response. The shelf-jump response test procedure follows that of Herman et. al., Comm. in Psychopharm., 3, pp. 165–171 (1979). A similar test procedure (Discrete Trial) in which a lever press was substituted for a shelf-jump was also used to establish the activity of the compound of Example 5. The compound was tested over a full dose range and the Avoidance Block activities reported as "$AB_{50}$'s (mg/kg): Shelf-jump: 6.43 (no CI) i.p., 58.28 (no CI) p.o.; Discrete Trial: 4.80 (2.14–17.66) i.p., 35.35 (no CI) p.o.

Hence, the compounds of this invention are useful in the treatment of various CNS disorders amenable to treatment with antipsychotic and anxiolytic agents. They may be administered neat or with a pharmaceutical carrier to a patient in need thereof by the attending physician. The pharmaceutical carrier may be a solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis or state of anxiety and the size, age and response pattern of the patient.

The following examples illustrate the production of representative compounds of this invention.

EXAMPLE 1

2-[4-[4-(1,2-Benzisothiazol-3-yl)-1-piperazinyl]butyl]-1H-isoindole-1,3(2H)-dione An 18.01 g sample of 1-(1,2-benzisothiazol-3-yl)piperazine (83.7 mmol), 29.5 g of N-(4-bromobutyl)phthalimide (104.6 mmol) and 36 mL of N,N-diisopropylethylamine (375.4 mmol) were added to 400 mL of dry DMF. The solution was heated at 80° C. for 18 hours, and the solvent was then removed in vacuo. The residue was dissolved in 500 mL of methylene chloride and was washed with saturated aqueous sodium bicarbonate. The combined aqueous layers were re-extracted with 2 portions of methylene chloride. The combined organic layers were dried over $Na_2SO_4$, filtered, and concentrated in vacuo. The residue was crystallized from isopropanol with the addition of 4N HCl/isopropanol to give 23.03 g of the title compound as the hydrochloride, quarter hydrate, m.p. 253°–255° C.

Anal. Calcd. for $C_{23}H_{24}N_4O_2S \cdot HCl \cdot \frac{1}{4}H_2O$: C, 59.85; H, 5.57; N, 12.14; Found: C, 59.84; H, 5.73; N, 12.14.

EXAMPLE 2

4-(1,2-Benzisothiazol-3-yl)-1-piperazinebutanamine

The compound prepared in Example 1 (13.00 g, 28.2 mmol) was converted to the freebase by washing a methylene chloride solution of the compound with saturated aqueous sodium bicarbonate. After drying over $Na_2SO_4$, filtration, and evaporation in vacuo, the residue was dissolved in 400 mL of methanol. To this solution was added 4 mL of hydrazine (124 mmol) and the reaction was refluxed overnight. The resulting solution was evaporated in vacuo. The residue was redissolved in methylene chloride and washed with aqueous sodium carbonate. The aqueous layer was re-extracted with 2 additional portions of methylene chloride. The combined organic layers were dried with $Na_2SO_4$, filtered and evaporated to yield 8.07 g of free base. A 1 g sample of free base was crystallized from isopropanol with the addition of 4N HCl in isopropanol to yield 500 mg of the title compound as the dihydrochloride hydrate, m.p. 262°–265° C.

Anal. Calcd. for $C_{15}H_{22}N_4S \cdot 2HCl \cdot H_2O$: C, 47.24; H, 6.87; N, 14.69; Found: C, 47.62; H, 6.48; N, 14.88.

EXAMPLE 3

2-[4-[4-(1,2-Benzisothiazol-3-yl)-1-piperazinyl]butyl]-4,4a,5,5a,6,6a-hexahydro-4,6-ethenocycloprop[f]isoindole-1,3(2H,3aH)-dione An 1.00 g (53 mmol) sample of hexahydro-4,6-ethenocycloprop[f]benzofuran-1,3(2H, 3aH)-dione and 1.64 g (5.3 mmol) of 4-(1,2-benzisothiazol-3-yl)-1-piperazinebutanamine were combined in 300 mL of xylenes. The mixture was refluxed under nitrogen overnight with water removal via a Dean-Stark trap. The solvent was then removed in vacuo to yield 2.99 g of residue. The product was column chromatographed by HPLC on silica with a gradient elution beginning with 10% hexane/ethyl acetate, then ethyl acetate, and finally 5% methanol/ethyl acetate. The product-containing fractions were combined and evaporated to yield 2.22 g of product. The residue was crystallized from isopropanol with the addition of 4N HCl in isopropanol to yield 2.03 g of the title compound as the dihydrochloride, m.p. 233°–235° C.

Anal. Calcd. for $C_{26}H_{30}N_4O_2S \cdot 2HCl$: C, 58.31; H, 6.02; N, 10.40; Found: C, 58.50; H, 5.90; N, 10.10.

EXAMPLE 4

2-[4-[4-(1,2-Benzisothiazol-3-yl)-1-piperazinyl]butyl]-3a,4,4a,6a,7,7a-hexahydro-4,7-etheno-1H-cyclobut[f]isoindole-1,3(2H)-dione An 2.02 g (10 mmol) sample of hexahydro-4,7-etheno-1H-cyclobut[f]isobenzofuran-1,3(2H)-dione and 3.10 g (10 mmol) of 4-(1,2-benzisothiazol-3-yl)-1-piperazineutanamine was combined in 300 mL of xylenes. The mixture was refluxed under nitrogen overnight with water removal via a Dean-Stark trap. The solvent was then removed in vacuo to yield 5.15 g of crude product. The product was column chromatographed by HPLC on silica with a gradient elution beginning with 10% hexane/ethyl acetate, then ethyl acetate, and finally 5% MeOH/ethyl acetate. The product-containing fractions were combined and evaporated to yield 4.35 g of product. The residue was crystallized from isopropanol with the addition of 4N HCl in isopropanol to yield 4.05 g of the title compound as the hydrochloride three quarter hydrate, m.p. 264°–266° C.

Anal. Calcd. for $C_{27}H_{30}N_4O_2S \cdot HCl \cdot \frac{3}{4}H_2O$: C, 61.81; H, 6.25; N, 10.68; Found: C, 61.82; H, 6.14; N, 10.50.

EXAMPLE 5

Decahydro-3-[4-[4-(1,2-benzisothiazol-3-yl)-1-piperazinyl]butyl]-1,5-methano-6,7,9-metheno-2H-pentaleno[1,2-d]azepine-2,4(3H)-dione An 2.3 g (10 mmol) of decahydro-1,5-methano-6,8,9-methenopentaleno-[1,2-d]oxepine-2,4-(1H,5H)-dione was added to 300 mL xylenes along with 3.28 g (10 mmol) of 4-(1,2-benzisothiazol-3-yl)-1-piperazinebutanamine. The mixture was refluxed under nitrogen overnight with water removal via a Dean-Stark trap. The solvent was then removed in vacuo to yield 5.49 g of crude material. The product was column chromatographed by HPLC on silica with a gradient elution beginning with methylene chloride and ending with 2% methanol in methylene chloride. The product-containing fractions were combined and evaporated to yield 1.40 g of product. The residue was crystallized from isopropanol with the addition of 4N HCl in isopropanol to yield 440 mg of the title compound as the hydrochloride hemihydrate, m.p. 215°–217° C.

Anal. Calcd. for $C_{29}H_{34}N_4O_2S \cdot HCl \cdot \frac{1}{2}H_2O$: C, 63.54; H, 6.62; N, 10.22; Found: C, 63.36; H, 6.49; N, 9.89.

EXAMPLE 6

(Exo)-octahydro-2-[4-[4-(1,2-benzisothiazol-3-yl)-1-piperazinyl]butyl]-4,5,7-metheno-1H-pentaleno[1,2-c]pyrrole-1,3(1H)-dione Octahydro-4,5,7-methenopentaleno[1,2-c]furan-1,3-dione (3.28 g, 20 mmol) was combined with 6.17 g (20 mmol) of 4-(1,2-benzisothiazol-3-yl)-1-piperazinebutanamine in 300 mL of xylene and refluxed under nitrogen overnight with a Dean-Stark trap. The solvent was removed in vacuum to yield 10.59 g of crude product. The residue was column chromatographed by HPLC on silica with a gradient elution beginning with 20% isopropanol in hexane and ending with 50% isopropanol/hexane. The exo and endo isomers were separated to yield 1.97 g and 4.76 g respectively. The exo product was crystallized from isopropanol with the addition of 4N HCl isopropanol to yield 1.46 g of the title compound as the hydrochloride, m.p. 220°–221° C.

Anal. Calcd. for $C_{26}H_{30}N_4O_2S \cdot HCl$: C, 62.57; H, 6.26; N, 11.23; Found: C, 62.43; H, 6.32; N, 11.19.

EXAMPLE 7

(Endo)-octahydro-2-[4-[4-(1,2-benzisothiazol-3-yl)-1-piperazinyl]butyl]-4,5,7-metheno-1H-pentaleno[1,2-c]pyrrole-1,3(2H)-dione The endo isomer from Example 6 was crystallized from isopropanol with the addition of 4N HCl isopropanol to yield 4.82 g of the title compound as the hydrochloride quarter hydrate, m.p. 263°–264° C.

Anal. Calcd. for $C_{26}H_{31}N_4O_2SCl \cdot \frac{1}{4}H_2O$: C, 62.01; H, 6.31; N, 11.13; Found: C, 62.01; H, 6.47; N, 10.95.

We claim:

1. The compounds of formula (I)

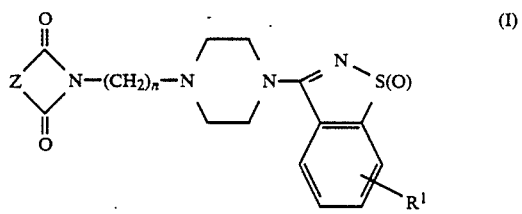

wherein $R^1$ is hydrogen, hydroxy, cyano, alkyl of 1 to 3 carbon atoms, alkoxy of 1 to 3 carbon atoms, halo or trifluoromethyl; (O) represents optional oxidation of sulfur; n is 2 to 5 and Z is

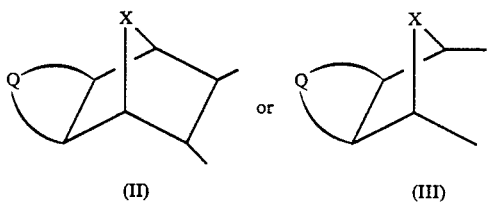

wherein X is alkylene of 1 to 4 carbon atoms or alkylidene of 2 to 4 carbon atoms; Q is alkylene of 1 to 4 carbon atoms, alkylidene of 2 to 4 carbon atoms, or or Z is

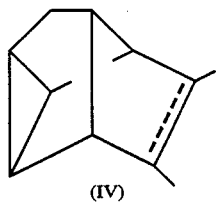 or 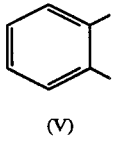

(IV)   (V)

or a pharmaceutically acceptable salt thereof.

2. The compounds according to claim 1 wherein R¹ is hydrogen, hydroxy, methoxy, bromo or chloro; n is 4; Z is (II) wherein X is ethenylene and Q is methylene or ethenylene; or Z is (III) wherein X is methylene and Q is

or Z is (IV) or (V) or a pharmaceutically acceptable salt thereof.

3. A compound of claim 2 which is decahydro-3-[4-[4-(1,2-benzisothiazol-3-yl)-1-piperazinyl]butyl]-1,5-methano-6,7,9-metheno-2H-pentaleno[1,2-d]azepine-2,4(3H)-dione or a pharmaceutically acceptable salt thereof.

4. A compound of claim 2 which is 2-[4-[4-(1,2-benzisothiazol-3-yl)-1-piperazinyl]butyl]-3a,4,4a,6a,7,7a-hexahydro-4,7-etheno-1H-cyclobut[f]isoindole-1,3(2H)-dione or a pharmaceutically acceptable salt thereof.

5. A compound of claim 2 which is 2-[4-[4-(1,2-benzisothiazol-3-yl)-1-piperazinyl]butyl]-4,4a,5,5a,6,6a-hexahydro-4,6-ethenocycloprop[f]isoindole-1,3(2H,3aH)-dione or a pharmaceutically acceptable salt thereof.

6. A compound of claim 2 which is 2-[4-[4-(1,2-benzisothiazol-3-yl)-1-piperazinyl]butyl]-1H-isoindole-1,3(2H)-dione or a pharmaceutically acceptable salt thereof.

7. A compound of claim 2 which is (exo)-octahydro-2-[4-[4-(1,2-benzisothiazol-3-yl)-1-piperazinyl]butyl]-4,5,7-metheno-1H-pentaleno[1,2-c]pyrrole-1,3(1H)-dione or a pharmaceutically acceptable salt thereof.

8. A compound of claim 2 which is (endo)-octahydro-2-[4-[4-(1,2-benzisothiazol-3-yl)-1-piperazinyl]butyl]-4,5,7-metheno-1H-pentaleno[1,2-c]pyrrole-1,3(2H)-dione or a pharmaceutically acceptable salt thereof.

* * * * *